United States Patent [19]
Choi et al.

[11] Patent Number: 5,808,082
[45] Date of Patent: Sep. 15, 1998

[54] METHOD OF PREPARING PHOSPHODIESTERASE IV INHIBITORS

[75] Inventors: Woo-Baeg Choi, North Brunswick, N.J.; Hywyn R. D. Churchill, Radford, Va.; Joseph E. Lynch, Plainfield, N.J.; Paul J. Reider, Westfield, N.J.; Ralph P. Volante, Cranberry, N.J.

[73] Assignee: Merck & Co., Inc., Rahway, N.J.

[21] Appl. No.: 837,733

[22] Filed: Apr. 22, 1997

Related U.S. Application Data

[60] Provisional application No. 60/016,839 May 8, 1996.
[51] Int. Cl.$^6$ .................................................. C07D 213/30
[52] U.S. Cl. ......................... 546/334; 546/330; 546/331; 546/332; 546/335; 546/337; 546/338; 546/339; 546/340; 546/342
[58] Field of Search ...................................... 546/330, 331, 546/332, 334, 335, 337, 338, 340, 342

[56] References Cited

FOREIGN PATENT DOCUMENTS

WO 94/14742  7/1994  WIPO .
WO 95/17386  6/1995  WIPO .

*Primary Examiner*—Patricia L. Morris
*Attorney, Agent, or Firm*—J. Antonio Garcia-Rivas; Valerie J. Camara; Mark R. Daniel

[57] ABSTRACT

A process for the preparation of Phosphodiesterase IV inhibitors is described. The process consists of eight chemical steps involving five isolations to prepare the title compound from readily available isovanillin in 35% overall yield (Scheme 1). The process is highlighted by: a) a highly diastereoselective Michael addition of phenyllithium using (1R, 2S) cis-aminoindanol as a chiral auxiliary, b) highly crystalline intermediates providing for efficient purifications, c) crystallization of the final compound as its CSA salt for excellent enantiomeric purity.

10 Claims, No Drawings

METHOD OF PREPARING PHOSPHODIESTERASE IV INHIBITORS

This application claims the benefit of U.S. Provisional Application Ser. No. 60/016,839, filed May 8, 1996.

BACKGROUND OF THE INVENTION

This application is directed to an improved process for making phosphodiesterase IV inhibitors such as those described in WO 94/14742, published Jul. 7, 1994.

Many hormones and neurotransmitters modulate tissue function by elevating intra-cellular levels of adenosine 3', 5'-cyclic monophosphate (cAMP). The role of cyclic AMP (cAMP) as a second messenger is well recognised. It is responsible for transducing the effects of a variety of extra-cellular signals, including hormones and neurotransmitters. The level of intracellular cAMP is regulated through both its synthesis by adenyl cyclases and degradation by cyclic nucleotide phosphodiesterases (PDE). PDEs form a family of at least seven enzyme isotypes (I–VII) which differ in their affinity for cAMP and/or cGMP, subcellular localisation and regulation (Beavo J. A. and Reifsnyder D. H. (1990) *Trends PhannacoL Sci.* 11 150–155; Conti M. et al., (1991) *Endocrine Rev.* 12 218–234). The clinical effects of a number of drugs can be rationalised on the basis of their selectivity for a particular PDE isotype. For example, the cardiotonic drugs milrinone and zaprinast are PDE III and PDE V inhibitors respectively. (Harrison S. A. et al., (1986) *Mol. Pharmacol.* 29 506–514; Gillespie P. G. and Beavo J. (1989) *Mol. Pharmacol.* 36 773–781). The anti-depressant drug, rolipram functions as a selective PDE IV inhibitor. (Schneider H. H. et al., (1986) *Eur. J. Phannacol* 127 105–115.).

The availability of PDE isotype selective inhibitors has enabled the role of PDEs in a variety of cell types to be investigated. In particular it has been established that PDE IV controls the breakdown of cAMP in many inflammatory cells, for example, basophils (Peachell P. T. et al., (1992) *J. Immunol.* 148 2503–2510) and eosinophils (Dent G. et al., (1991) *Br. J. Phannacol.* 103 1339–1346) and that inhibition of this isotype is associated with the inhibition of cell activation. Consequently PDE IV inhibitors are currently being developed as potential anti-inflammatory drugs particularly for the prophylaxis and treatment of asthma.

A prior art process is shown in the following reaction scheme

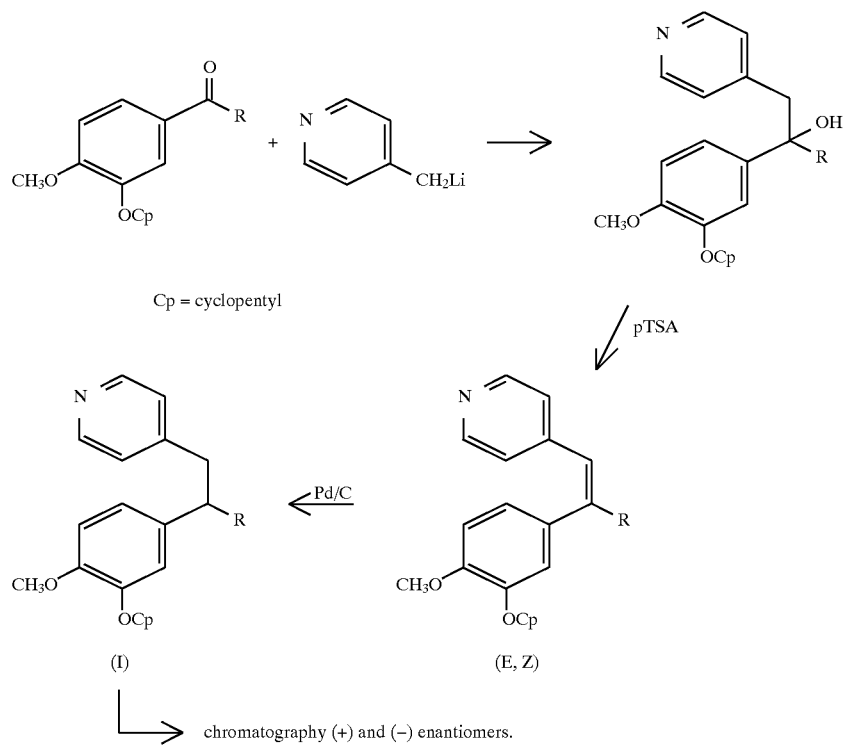

Cp = cyclopentyl chromatography (+) and (−) enantiomers.

This process, involving resolution into the enantiomers as a last step necessarily means a commerically unacceptable yield of product.

Another prior art process employs a synthetic strategy using 2S-bomane-10,2-sultam as a chiral auxiliary as shown below:

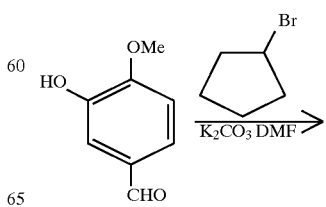

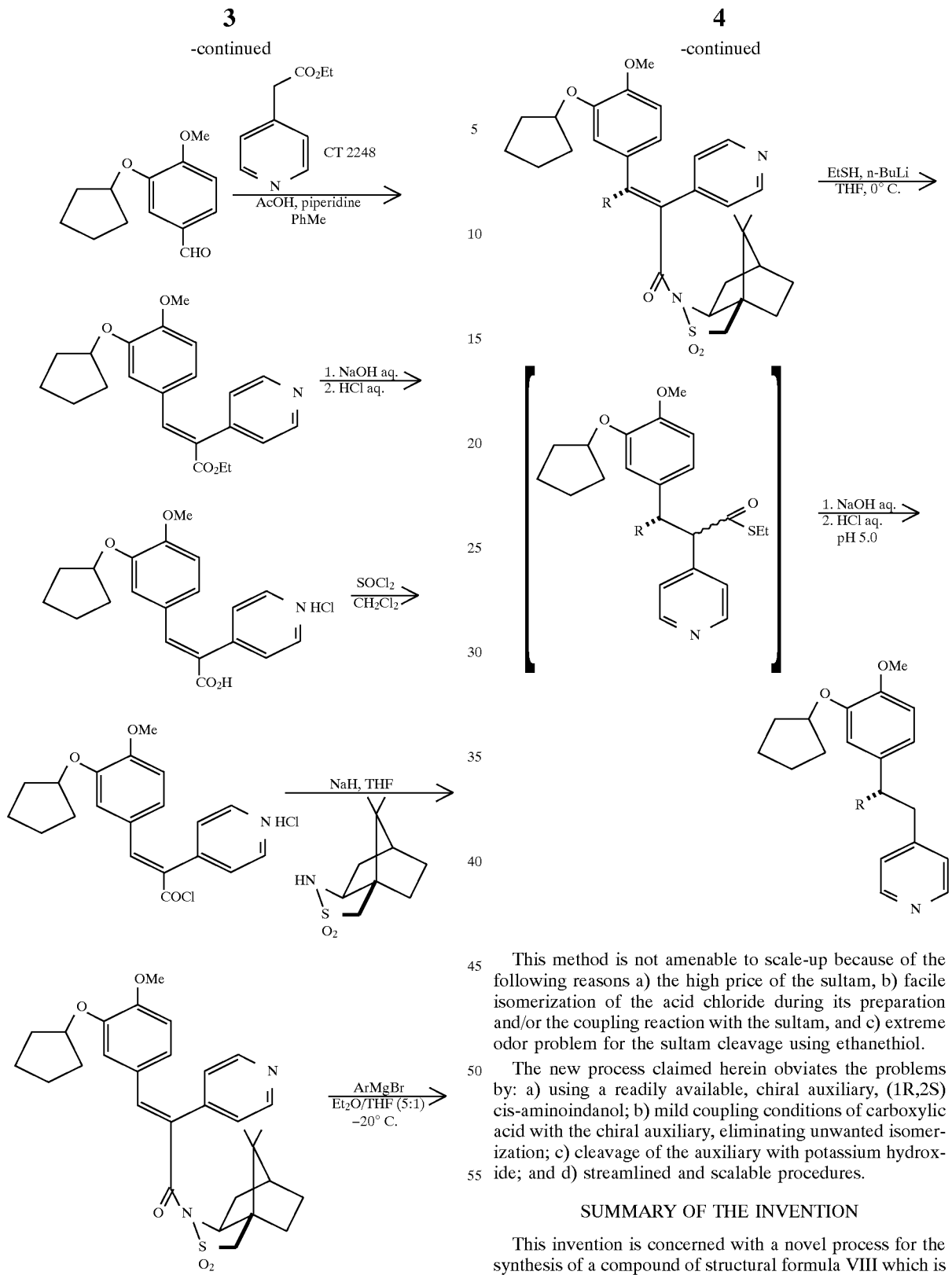

This method is not amenable to scale-up because of the following reasons a) the high price of the sultam, b) facile isomerization of the acid chloride during its preparation and/or the coupling reaction with the sultam, and c) extreme odor problem for the sultam cleavage using ethanethiol.

The new process claimed herein obviates the problems by: a) using a readily available, chiral auxiliary, (1R,2S) cis-aminoindanol; b) mild coupling conditions of carboxylic acid with the chiral auxiliary, eliminating unwanted isomerization; c) cleavage of the auxiliary with potassium hydroxide; and d) streamlined and scalable procedures.

SUMMARY OF THE INVENTION

This invention is concerned with a novel process for the synthesis of a compound of structural formula VIII which is a PDE IV inhibitor useful in the prophylaxis and treatment of asthma:

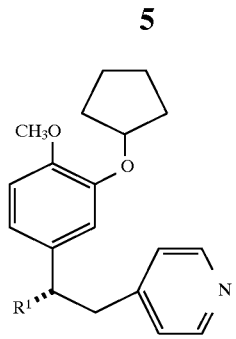

VIII

The overall process consists of eight chemical steps involving five isolations to prepare the title compound from readily available isovanillin in 35% overall yield. The process is highlighted by: a) a highly diastereoselective Michael addition of phenyllithium using (1R, 2S) cis-aminoindanol as a chiral auxiliary; b) highly crystalline intermediates providing for efficient purifications; and c) crystallization of the final compound as its CSA salt for excellent enantiomeric purity.

DETAILED DESCRIPTION OF THE INVENTION

The novel process of this invention can be depicted by the following reaction scheme:

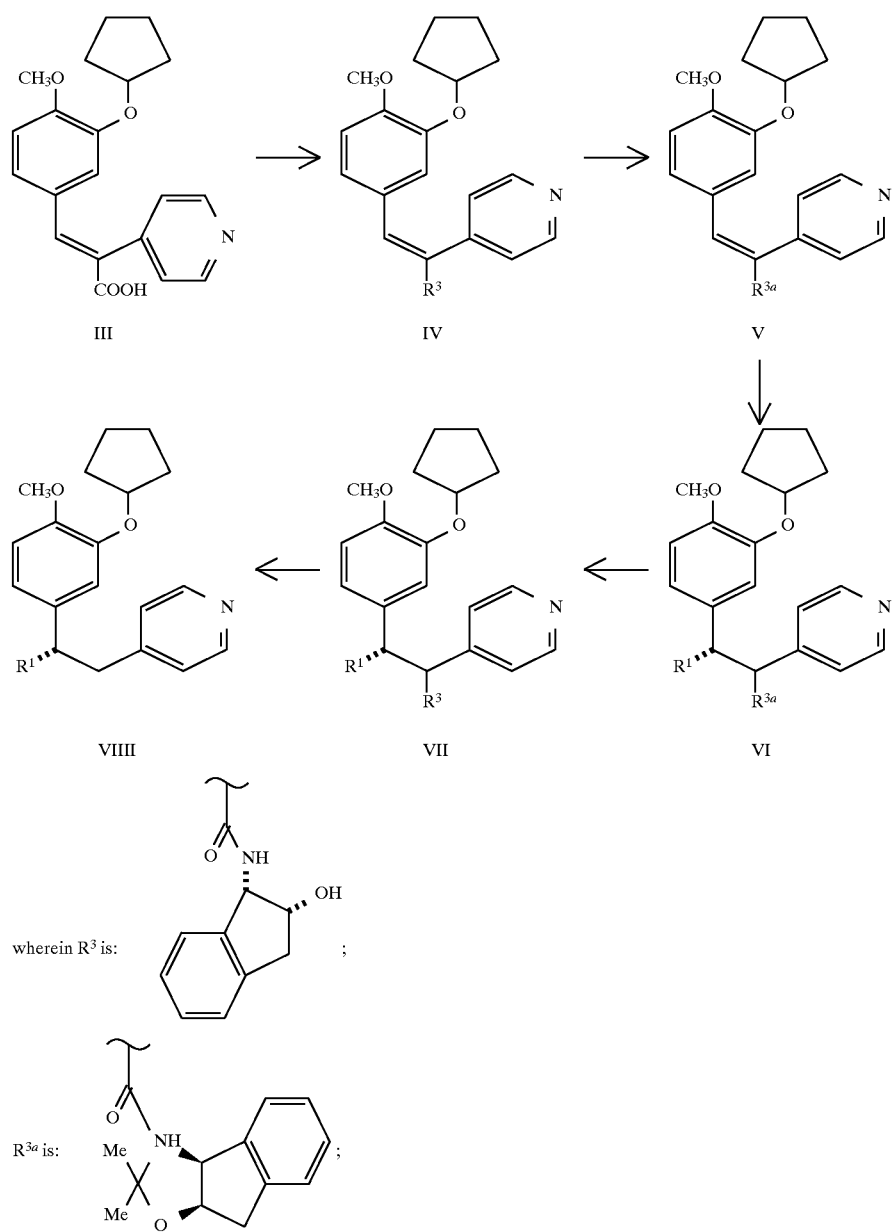

$R^1$ is phenyl, either unsubstituted or substituted with one or two substituents, which can be the same or different, selected from the group consisting of $R^2$ and $Alk^1(R^2)m$ wherein:

$R^2$ is:
1) —halo,
2) —N($R^4$)$_2$,
3) —NO$_2$,
4) —CN,
5) —O$R^4$,
6) —C$_{3-6}$ cycloalkoxy,
7) —CO($R^4$),
8) —COO$R^4$,
9) —S$R^4$,
10) —SO$_3$H,
11) —SO$_2$($R^4$),
12) —SO$_2$N($R^4$)$_2$,
13) —CON($R^4$)$_2$,
14) —NHSO$_2$$R^4$,
15) —N(SO$_2$$R^4$)$_2$,
16) —NHSO$_2$N($R^4$)$_2$,
17) —NHCO$R^4$ or
18) —NHCOO$R^4$; wherein:

$Alk^1$ is: straight or branched chain C$_{1-6}$ alkylene, C$_{2-6}$ alkenylene or C$_{2-6}$ alkynylene, optionally interrupted by one, two or three —O—, —S—, —S(O)p or —N($R^4$)—;

$R^4$ is: hydrogen or C$_{1-6}$ alkyl;

m is: zero or an integer selected from 1, 2 and 3; and p is: an integer selected from 1 and 2.

The novel process comprises the steps of:

(a) coupling a compound of formula III:

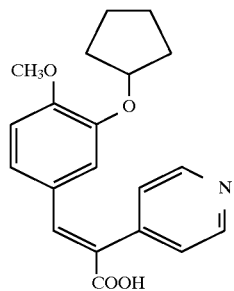

with (1R,2S) cis-aminoindanol in an aprotic solvent in the presence of one or more amide coupling reagents to yield a compound of formula IV:

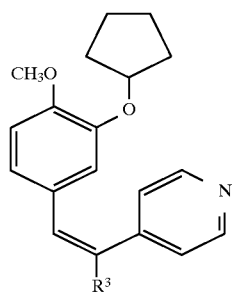

wherein $R^3$ is:

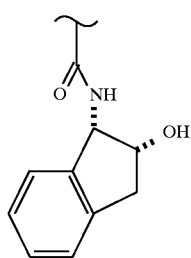

For purposes of this specification the aprotic solvent includes, but is not limited to ethereal solvents such as diethyl ether, di-n-butyl and di-isopentyl ethers, anisole, cyclic ethers such as tetrahydropyran, 4-methyl-1,3-dioxane, tetrahydrofurfuryl methyl ether, furan, and tetrahydrofuran as well as ester solvents such as C$_{1-6}$alkyl esters including ethyl acetate and isopropyl acetate.

For purposes of this specification, amide coupling reagents are defined to include, but are not limited to hydroxy benzotriazole (HOBT) and di-cyclohexylcarbodiimide (DCC).

The reaction step (a) is allowed to proceed until substantially complete in 5 to 25 hr. The molar ratio of compound III to cis-aminoindanol and compound III to each amide coupling reagent is typically 0.5:1 to 1:1. An excess of cis-aminoindanol and coupling reagent is generally prefered. It is preferred that both DCC and HOBT are used. In that instance, the ratio of DCC to HOBT is typically 0.8:1 to 1:0.8. The reaction may be conducted at 5° to 50° C.; preferably 15° to 25° C.

(b) Reacting a compound of formula IV with 2-methoxypropene and methanesulfonic acid in an aprotic solvent to yield a compound of formula V:

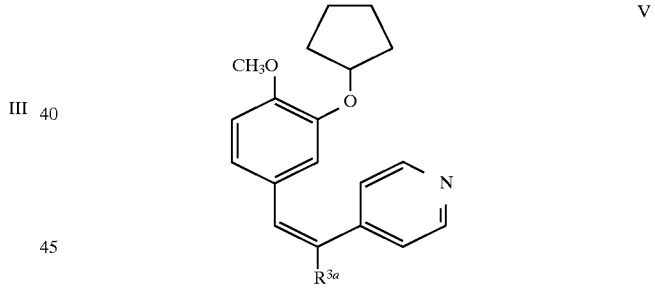

wherein $R^{3a}$ is:

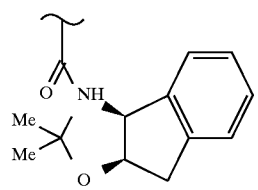

For purposes of this specification the aprotic solvent includes, but is not limited to ethereal solvents as defined above.

The reaction step (b) is allowed to proceed until substantially complete in 15 min. to 2 hr. The molar ratio of formula IV to 2-methoxypropene and methanesulfonic acid is 0.8: 1 to 1:1.2. An excess of methanesulfonic acid is generally prefered. The reaction may be conducted at 5° to 50° C.; preferably 15° to 25° C.

(c) Reacting, by conjugate addition, a compound of formula V with a compound of the formula:

(a) Li R¹,
(b) R¹MgX, wherein X is halo,
(c) Li (R¹)₂Cu, or
(d) Li₂R¹CuCnX in an aprotic solvent to yield, after acidification a compound of formula VI:

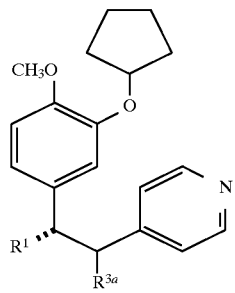

VI

For purposes of this specification the aprotic solvent includes, but is not limited to ethereal solvents as described above.

The reaction step (c) is allowed to proceed until substantially complete in 5 to 30 min. The molar ratio of formula V to (a) Li R¹,
(b) R¹MgX, wherein X is halo,
(c) Li (R¹)₂Cu, or
(d) Li₂R¹CuCnX is 0.8:1 to 1:1.2. An excess of lithium compound is generally prefered. The reaction may be conducted at −70° to −35° C.; preferably −45° to −50° C.

(d) Reacting an amide of formula VI with a strong acid in a hydrolytic solvent to yield, after neutralization, a compound of formula VII:

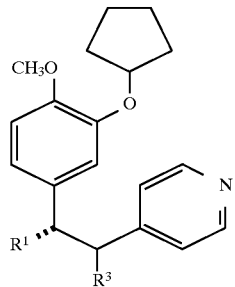

VII

For purposes of this specification the strong acid is defined to include mineral acids, such as HCl and H₂SO₄ as well as strong organic acids such as CF3COOH and sulfonic acids including methane, toluene and benzene sulfonic acid. For purposes of this specification the hydrolytic solvent shall include H₂O and alcohols such as C$_{1-6}$alkanols. Neutralization may be accomplished by addition of any suitable base, including sodium or potassium hydroxide, carbonate, bicarbonate and amonium hydroxide.

The reaction is allowed to proceed until substantially complete in 15 minutes to 3 hours. The reaction is conducted at 0° to 50° C. The molar ratio of formula VII to acid (and base) is 1:1 to 1:6. Preferably, excess acid and excess base are used.

(e) Hydrolysis of compound VII with a strong base in a non-reactive water soluble organic solvent to yield a compound of formula VIII:

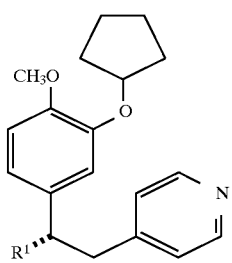

VIII

For purposes of this specification, the base includes both organic bases including pyridine, tri-C$_{1-3}$ alkylamine, and inorganic bases include sodium hydroxide, potassium hydroxide, sodium carbonate or bicarbonate or potassium carbonate or bicarbonate.

For purposes of this specification the non-reactive water soluble solvent is intended to include, but is not limited to ethylene glycol, C$_{1-6}$alkanol, such as methanol, ethanol, isopropanol, and t-butyl alcohol.

The reaction step (e) is allowed to proceed until substantially complete in 5 to 25 hr. The molar ratio of compound VII to base is 1:1. Typically excess base is used resulting in a ratio of formula VII to base of about 1:5 to 1:10. The reaction may be conducted at 25° to 200° C.; preferably 140° to 170° C.

The following abbreviations have the indicated meanings:

AA=arachidonic acid
Ac=acetyl
AIBN=2.2-azobisisobutyronitrile
Bn=benzyl
CMC=1-cyclohexyl-3-(2-morpholinoethyl) carbodiimidemetho-p-toluenesulfonate
DBU=diazabicyclo[5.4.0]undec-7-ene
DCC=di-cyclohexylcarbo-diimide
DMAP=4-(dimethylamino)pyridine
DMF=N,N-dimethylformamide
DMSO=dimethyl sulfoxide
Et₃N=triethylamine
HOBT=hydroxy benzotriazole
KHMDS=potassium hexamethyldisilazane
LDA=lithium diisopropylamide
mCPBA=metachloro perbenzoic acid
MMPP=magnesium monoperoxyphthalate
Ms=methanesulfonyl=mesyl
MsO=methanesulfonate=mesylate
NBS=N-bromosuccinimide
NCS=N-chlorosuccinimide
NIS=N-iodosuccinimide
Oxone®=potassium peroxymonosulfate
PCC=pyridinium chlorochromate
PDC=pyridinium dichromate
r.t.=room temperature
rac.=racemic
Tf=trifluoromethanesulfonyl=triflyl
TFAA=trifluoroacetic anhydride
TfO=trifluoromethanesulfonate=triflate
THF=tetrahydrofuran
TLC=thin layer chromatography
TMPD=N,N,N',N'-tetramethyl-p-phenylenediamine
Ts=p-toluenesulfonyl=tosyl
TsO=p-toluenesulfonate=tosylate Tz=1H (or 2H)-tetrazol-5-yl
Alkyl group abbreviations Dose Abbreviations
- Me =methyl
- Et =ethyl
- n-Pr =normal propyl
- i-Pr =isopropyl
- n-Bu =normal butyl
- i-Bu =isobutyl
- s-Bu =secondary butyl
- t-Bu =tertiary butyl
- c-Pr =cyclopropyl
- c-Bu =cyclobutyl
- c-Pen =cyclopentyl
- c-Hex =cyclohexyl Dose Abbreviations
- bid =bis in die=twice daily
- qid =quarter in die=four times a day
- tid =ter in die=three times a day For purposes of this specification "Alkyl" means linear and branched structures containing the indicated number of carbon atoms. Examples of alkyl groups include methyl, ethyl, propyl, isopropyl, butyl, s- and t-butyl, pentyl and hexyl.

For purposes of this specification "Halo" means F, Cl, Br, or I.

The Following examples are intended to illustrate, but not limit the invention as disclosed herein:

EXAMPLE 1

Step 1: Cyclopentylation/Condensation

I → II

Mw = 152.15          Mw = 367.45
$C_8H_8O_3$          $C_{22}H_{25}NO_4$

| | | | |
|---|---|---|---|
| isovanillin (Mw = 152.15) | 138.15 g | 0.91 mol | |
| potassium carbonate (Mw = 138.21) | 238.5 g | 1.72 mol | 1.90 eq. |
| cyclopentyl bromide (149.04/1.390) | 185 mL | 1.72 mol | 1.90 eq. |
| DMF | 0.8 L | | KF = 100 |
| toluene | 1.5 L | | |
| hydrochloric acid, 1N (aq.) | 0.8 L | | |
| water | 2.4 L | | |
| ethyl 4-pyridylacetate (Mw = 165.19) | 150 g | 0.91 mol | |
| acetic acid (60.05/1.05) | 30.8 ml | 0.54 mol | 0.60 eq. |
| piperidine (85.15/0.861) | 10.3 ml | 0.104 mol | 0.11 eq. |
| sat. sodium bicarbonate (aq.) | 1.0 L | | |
| ethyl acetate | 0.6 L | | |
| THF | 0.1 L | | |
| florisil | 20 g | | |
| activated carbon, Darco KB | 15 g | | 5 W % |
| hexanes | 2.4 L | | |

Isovanillin and potassium carbonate were added to DMF (0.8 L) portionwise at RT. The mixture was heated to 60° C. and cyclopentyl bromide was added over 30 min at 60° C. The mixture was aged at 60° C. for 14 h.

The mixture was cooled to RT and water (1.2 L) was added in one portion. The solution was stirred for 30 min. The mixture was extracted twice with toluene (1 L, 0.5 L). The combined organic layers were washed with hydrochloric acid (0.8 L) and twice with water (0.6 L×2). The organic layer was concentrated to 1 L in volume. This solution was used for the next step directly.

Ethyl 4-pyridylacetate, acetic acid (21.8 mL, 0.38 mol), and piperidine (7.3 mL, 0.074 mol) were added consecutively to the aldehyde/toluene solution at RT. The solution was refluxed for 4 h with a Dean-Stark trap. Additional acetic acid (9 ml) and piperidine (3 ml) were added and the solution was refluxed for an additional 14 h.

The solution was allowed to cool to 35° C. and was washed with sodium bicarbonate solution (1.0 L), followed by water twice (0.6 L×2). The resulting solution was stirred with charcoal (15 g) for 1 h at RT.

Ethyl acetate (0.6 L) and THF (0.1 L) were added during the extraction to solublize all the product.

The slurry was filtered through a pad of florisil and concentrated to about 0.9 L in volume. Hexanes (1.4 L) was added at RT, and the mixture was cooled to 0° C. and aged for 30 min at 0° C. The product was collected by a suction filtration as a yellowish brown solid, washed with hexanes (1 L), and dried at 50° C. for 24 h to give 254.9 g (0.694 mol, 76.3% yield).

Product crystallized out during the concentration.

Estimated toluene volume after the concentration was ca. 600 mL.

Total crystallization volume: 2.3 L.

Supernatant conc. at 0° C.: 25 g/L

Assay yield: 93%.

Mother liquor loss: 17%.

Step 2: Ethyl Ester Hydrolysis

II → III

Mw = 367.45          Mw = 339.39
$C_{22}H_{25}NO_4$   $C_{20}H_{21}NO_4$

| | | | |
|---|---|---|---|
| ethyl ester (II) | 254.9 g | 0.694 mol | |
| sodium hydroxide, 5N (aq.) | 257 mL | 1.28 mol | 1.84 eq. |
| THF | 1.5 L | | |
| hydrochloric acid, 2N (aq.) | 640 mL | 1.28 mol | |
| ethyl acetate | 1.7 L | | |
| hexanes | 1.5 L | | |
| water | 0.75 L | | |

The ethyl ester was dissolved in THF (1.5 L) at RT. Sodium hydroxide aq. solution (5N, 257 mL) was added portionwise at RT. The solution was heated to reflux for 4–6 h.

The solution was cooled to 30° C. and neutralized with hydrochloric acid (2N, 640 mL) to pH 6.

Base addition was slightly exothermic.

Sodium hydroxide (2 mL) was added to adjust the pH to 6.

Internal temperature was maintained between 30° C. and 40° C. to keep most of product in solution.

The solution was extracted twice with ethyl acetate (1.5 L, 0.2 L). The combined organic solution was washed with water (0.75 L) and concentrated at atmospheric pressure to about 0.9 L.

Boiling temperature sharply rose from 66° C. to 76° C. near the end of concentration, and crystallization took place during the concentration.

The mixture was cooled to 30° C. and hexanes (0.9 L) were added. The slurry was allowed to cool to RT and aged overnight. The product was collected by suction filtration as a pink crystalline solid, washed with 1:3 ethyl acetate:hexanes (0.8 L) and dried in vacuo at 50° C. for 6 h to give 235.3 g (0.693 mol, 100% yield).

Mother liquor loss: 0.7%.

ethyl acetate (1 L) was added to the organic layer to get the layer separation during the 2nd water wash.

The organic layer was concentrated in the batch concentrator to about 1 L in volume. The solution contained some solids (DCU) and water droplets. Thus, the mixture was washed with half brine (0.5 L water and 0.5 L sat. brine) and was filtered through a sintered glass funnel.

The organic layer was then concentrated to ca. 1 L in volume.

Ethyl acetate (1.5 L) and hexanes (1 L) were added and the mixture was aged overnight at RT. Additional hexanes (1.25 L) was added and the slurry was aged at RT for 1 h. The mixture was cooled to −6°—−10° C. and aged for 1 h. The product was collected as a white crystalline solid by filtration, washed with 1:3 ethyl acetate:hexanes (1 L) and dried in vacuo at 50° C. for 72 h to give 259.85 g (0.552 mol, 79.6 % yield). Mother liquor loss was 8%.

Step 3: Aminoindanol Coupling

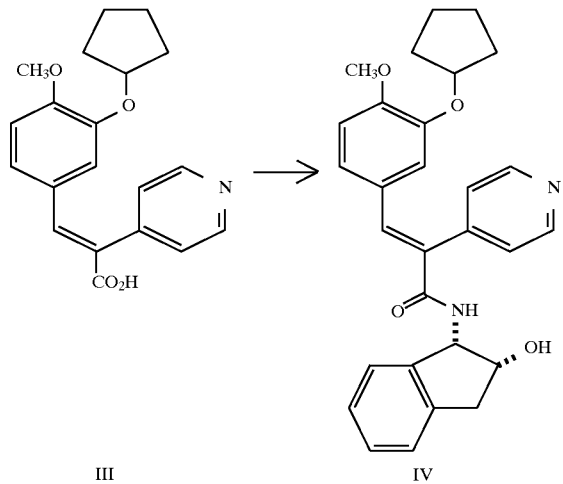

| III | IV |
|---|---|
| Mw = 339.39 | Mw = 470.57 |
| $C_{20}H_{21}NO_4$ | $C_{29}H_{30}N_2O_4$ |

| acid (III) | 235.5 g | 0.694 mol | |
| 1R,2S cis-aminoindanol | 124.1 g | 0.833 mol | 1.2 eq. |
| HOBT (Mw = 135.13) | 112.5 g | 0.833 mol | 1.2 eq. |
| DCC (Mw = 206.33) | 157.5 g | 0.763 mol | 1.1 eq. |
| THF | 2.7 L | | |
| ethyl acetate | 5.05 L | | |
| sodium carbonate water | 106 g | 1 mol | in 1.5 L |
| sat. sodium chloride (aq.) | 0.5 L | | |
| water | 2.5 L | | |
| hexanes | 3 L | | |

The acid was suspended in THF (2.5 L) and cis-aminoindanol was added in one portion at RT. HOBT was added portionwise and the mixture was aged for 10 min. Finally DCC was added and the solution was aged for 16 h at RT.

The slurry was cooled to 0° C., aged for 30 min, and filtered. The solids were washed with cold THF (0.2 L) and ethyl acetate (0.3 L). The filtrate was diluted with ethyl acetate (1 L) and was washed with sodium carbonate solution (1.5 L) and with water (1 L×2). The reaction mixture was filtered at 0° C. to remove the by-product DCU. More Step 4: Acetonization

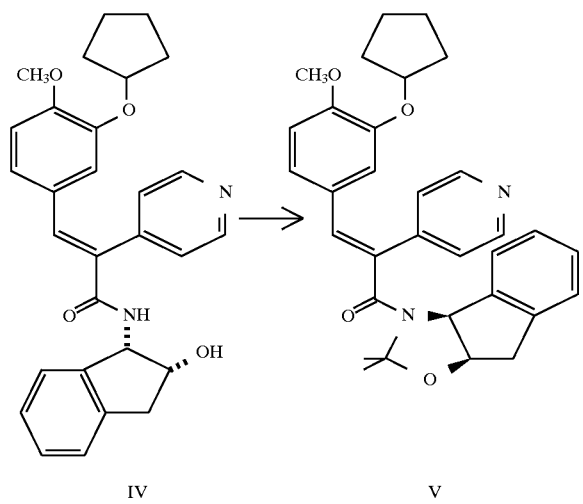

| IV | V |
|---|---|
| Mw = 470.57 | Mw = 510.632 |
| $C_{29}H_{30}N_2O_4$ | $C_{32}H_{34}N_2O_4$ |

| unsaturated amide-alcohol (IV) | 235.3 g | 0.5 mol | |
| 2-methoxypropene | 240 ml | 5.0 mol | 10 eq. |
| methanesulfonic acid | 32.4 ml | 0.5 mol | 1 eq. |
| THF | 3.5 L | | |
| sodium hydroxide, 5N (aq.) | 0.1 L | 0.5 mol | |
| water | 4.5 L | | |
| toluene | 3.9 L | | |

The amide-alcohol was dissolved in THF (3.5 L) at RT. 2-methoxypropene and methanesulfonic acid were added portionwise, consecutively. The solution was aged for 30 min.

The addition of acid was slightly exothermic, requiring a cooling bath to maintain a temperature below 30° C. The reaction was monitored by HPLC Condition 1 and proceeded to completion (<0.5 A % SM).

Vigorous stirring was required to maintain a stirrable slurry.

The thick slurry was transferred portionwise into a sodium hydroxide/water (0.5 L) solution at RT. The mixture was extracted with toluene (3.5 L) and the layers were separated. The organic layer was washed with water (1.5 L) and concentrated to ca. 1.2 L in vacuo and held for the next reaction.

The basic quench solution must maintain a pH >8 to avoid hydrolysis of the acetonide. The quench is not exothermic.

The KF of the concentrated solution was 380 μg/mL (4 mol % water).

Step 5: Phenyl Addition

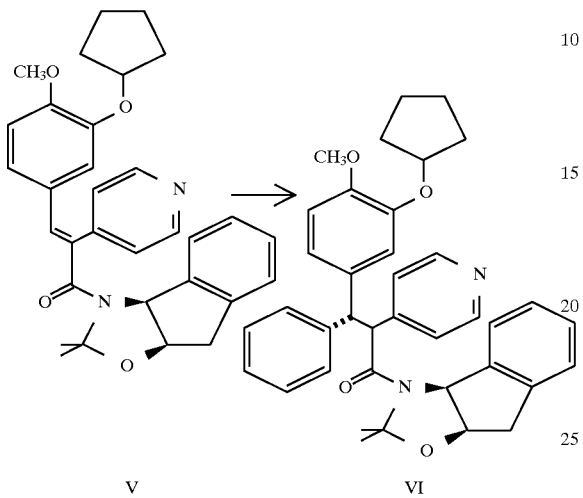

V

Mw = 510.632
$C_{32}H_{34}N_2O_4$

VI

Mw = 588.745
$C_{38}H_{40}N_2O_4$

| | | |
|---|---|---|
| olefin-acetonide in toluene | ca. 1.2 L | ca. 0.5 mol |
| phenyllithium, 1.8M solution in cyclohexane:ether (7:3) | 305 ml | 0.55 mol |
| THF | 1.25 L | |
| hydrochloric acid, 2N (aq.) | 325 ml | 0.65 mol |
| water | 4.0 L | |
| toluene | 2.0 L | |
| methanol | 5.7 L | |

The acetonide in toluene was diluted with THF (1.2 L) and cooled to −45° C. The phenyllithium solution was added over 20 min, maintaining an internal temperature of below −35° C. The solution was aged for 30 min at −35°–45° C.

Phenyllithium is pyrophoric and reacts vigorously with water! The reaction was monitored by HPLC Condition 2 and proceeds to completion (<0.2 A % SM).

The solution was neutralized with hydrochloric acid to pH 7. Water (2 L) was added and the mixture was aged for 15 min. The mixture was extracted with toluene (2 L) and the layers were separated. The organic layer was washed with water (2 L) and transferred to a batch concentrator, using THF (0.5 L) as rinse. The solution was concentrated to ca. 1 L in vacuo by addition/distillation at 35° C. Methanol (5 L) was used to remove toluene by azetropic distillation. The final volume of the batch after the distillation was ca. 1.8 L. Additional methanol (0.7 L) was added and the solution was held for the next reaction.

The final solution contained <5% toluene.

The final volume: 2.5 L

Step 6: Deacetonization

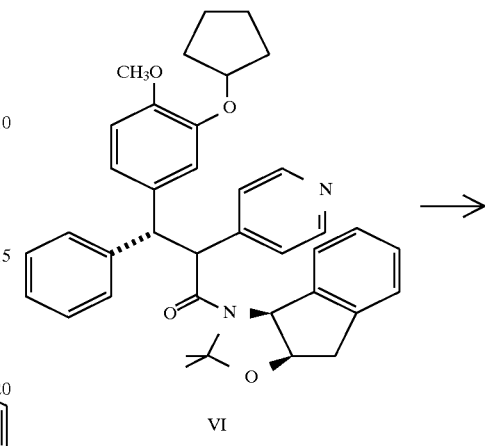

VI

Mw = 588.745
$C_{38}H_{40}N_2O_4$

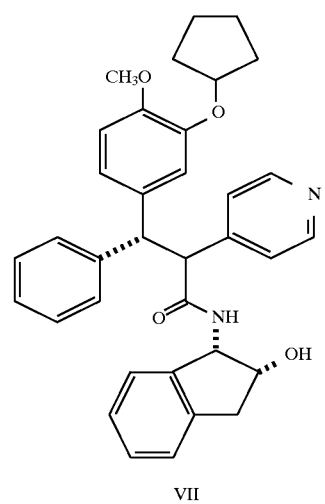

VII

Mw = 548.683
$C_{35}H_{36}N_2O_4$

| | | | |
|---|---|---|---|
| adduct in methanol | 2.5 L | ca. 0.5 mol | |
| hydrochloric acid (g); (Mw = 35.5) | 120 g | 3.30 mol | 6.6 eq. |
| sodium hydroxide, 5N (aq.) | 610 mL | 3.05 mol | 6.0 eq. |
| water | 2.5 L | | |

Hydrochloric acid gas was bubbled vigorously into the Michael adduct-acetonide/methanol solution at <40° C. over 30 min. The solution was aged for 1 h at RT.

The acid bubbling was exothermic, requiring an ice/water bath to maintain a temperature below 40° C. The reaction was monitored by HPLC Condition 1 and proceeded to completion (<0.5 A % SM).

The slurry was neutralized with sodium hydroxide solution (5N, 610 mL) below 30° C. to pH 6.5.

The neutralization was exothermic, requiring an external cooling bath to maintain a temperature below 40° C.

Water (2.5 L) was added and the slurry was aged for 1 h. The product was collected by a filtration as a sandy-brown solid, washing with water (0.5 L) and dried in vacuo at 60° C. for 48 h to give 290.5 g (79% yield).

The product contained 25 W % sodium chloride. The effective yield is 218 g.

(79%) for the above three steps.

Mother liquor loss: 0.5%.

Step 7: Aminoindanol Hydrolysis

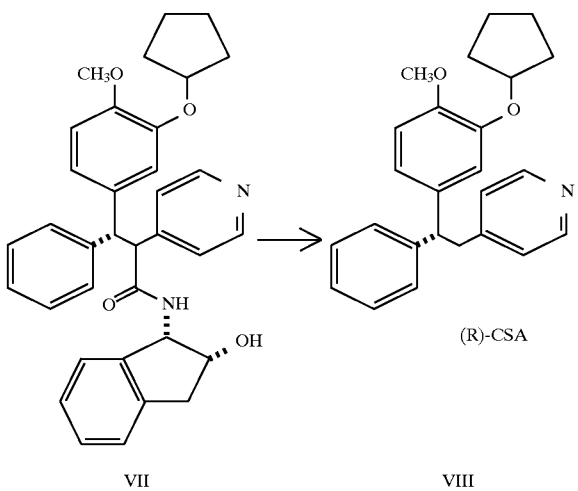

| Michael adduct-amide, 75 W % | 273.9 g | 0.374 mol | 25 W % NaCl |
|---|---|---|---|
| potassium hydroxide (Mw = 56.11) | 210 g | 3.74 mol | 10 eq. |
| ethylene glycol | 2.66 L | | |
| hydrochloric acid, 2N (aq.) | 1.8 L | 3.6 mol | |
| sodium hydroxide, 5N (aq.) | 120 mL | 0.6 mol | |
| ethyl acetate | 6.0 L | | |
| water | 7.0 L | | |
| activated carbon, Darco KB | 40 g | | 20 W % |
| florisil | 480 g | | |
| seed | 5 g | | 2% |
| (1R)-10-CSA (Mw = 232.30) | 87 g | 0.374 mol | |
| hexanes | 1.65 L | | |

The amide and potassium hydroxide pellets were suspended in ethylene glycol at RT. The mixture was heated to 160° C. and aged for 15 h. The solution was cooled to 40° C. and neutrallized to pH 6.5.

The reaction was monitored by HPLC Condition 2 and proceeded to completion.

(<0.5 A % SM).

First, HCl aq. solution (2N, 1.8 L) was added resulting in a pH of 1. Thus, sodium hydroxide aq. solution (5N, 120 mL) was added to adjust the pH to 6.5. A discrepancy in the amount of the base was unaccountable.

The addition of HCl was exothermic, requiring an ice/water bath to maintain a temperature below 40° C.

The mixture was diluted with water (3 L) and ethyl acetate (4 L). The layers were separated after mixing for 15 min. The organic layer was washed with water (2 L×2). Activated carbon was added to the organic layer and the solution was heated to 60° C. and aged for 1h. The solution was cooled to 35° C. and filtered through a pad of florisil, using ethyl acetate (2 L) for washings. The solution was concentrated at 40° C. in vacuo to ca. 0.75 L.

The carbon treatment removed solids and polar impurities, but does not result in a colorless solution.

(R)-CSA was dissolved in ethyl acetate (0.7 L) at 70° C. and added in one portion to the product solution. Flask was rinsed with ethyl acetate (0.1 L) at 70° C. and the rinse was added to the mixture. The solution was cooled to RT, seeded (5 g), and allowed to crystallize over 72 h. The slurry was then cooled to 0° C. and aged for additional 20 h. Hexanes (0.15 L) was added and the slurry was aged for 20 h. Additional hexanes (0.3 L) was added and the slurry was aged 4 h. Additional hexanes (0.45 L) was added and the slurry was aged for 20 h. The product was collected by suction filtration as a white, crystalline solid, washed with 1:1 ethyl acetate:hexanes (0.5 L), followed by hexanes (0.5 L) and dried for 48 h at 50° C./27 inHg to give 163.8 g CDP-840/CSA salt (72.3% yield, 99.6% ee).

Final solvent composition was 1:1 ethyl acetate/hexanes.

The enantiomeric purity was evaluated by chiral HPLC.

Assay yield: 95%

Mother liquor loss: 23%.

Step 8: F.$H_2SO_4$ Salt Formation

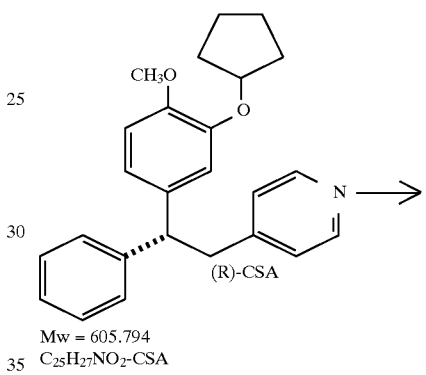

Mw = 605.794
$C_{25}H_{27}NO_2$-CSA

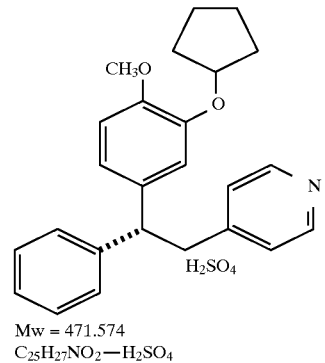

Mw = 471.574
$C_{25}H_{27}NO_2$—$H_2SO_4$

| CSA salt | 15.2 g | 25 mmol |
|---|---|---|
| 0.25M aq. NaOH | 200 mL | 50 mmol |
| MTBE | 200 mL | |
| Abs. EtOH | 180 mL | |
| conc. $H_2SO_4$ | 1.4 mL | 26.3 mm |

The CSA salt was partitioned between aq. NaOH (0.25N, 200 mL) and MTBE (200 mL). The organic layer was separated, washed with water (100 mL×2), and concentrated to dryness. The resulting oil was diluted with EtOH (50 mL) and concentrated. This was repeated twice. The resulting oil was dissolved in EtOH (50 mL), and the solution was treated with conc. sulfuric acid (0.7 mL, 0.5 eq.), seeded (50 mg), and aged for 2 h at RT. Additional conc. sulfuric acid (0.7 mL) was added and the mixture was aged for 2 h. Resulting solids were collected by filtration, washed with ethanol (30 mL), dried to give a white solid (10.67 g, 21.21 mmol, 83% yield, R:S 99.73:0.27) as 6.3 W % ethanol solvate.

EXAMPLE 2

4-[2-(3-cyclopentyloxy-4-methoxyphenyl)-1-(4-aminophenyl)-ethyl]pyridine

Step 1: Acetonide Formation

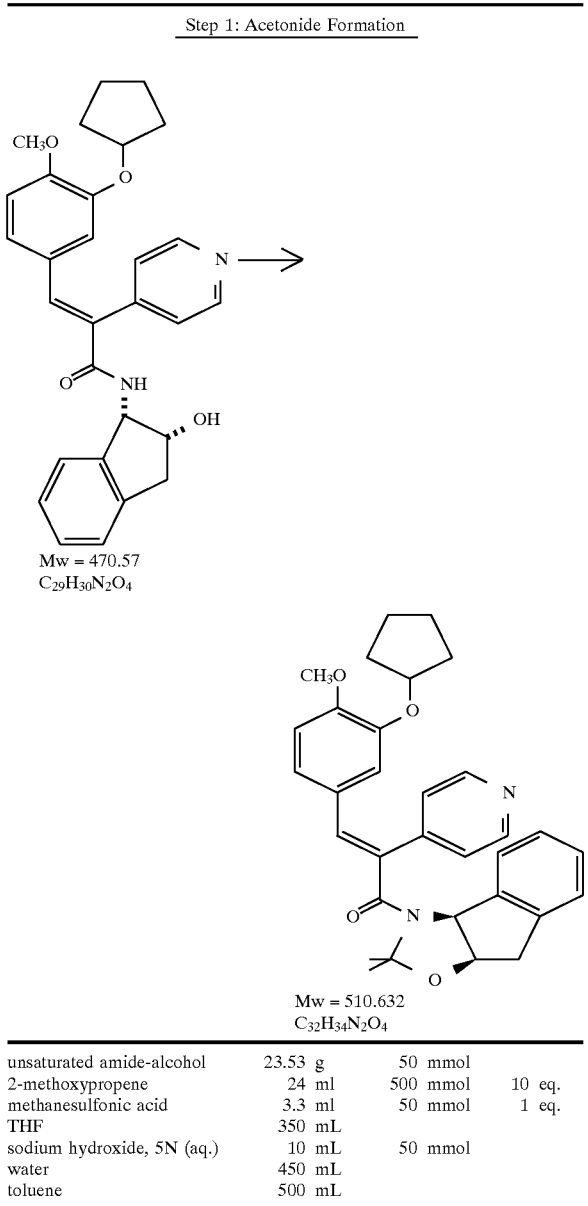

| | | | |
|---|---|---|---|
| unsaturated amide-alcohol | 23.53 g | 50 mmol | |
| 2-methoxypropene | 24 ml | 500 mmol | 10 eq. |
| methanesulfonic acid | 3.3 ml | 50 mmol | 1 eq. |
| THF | 350 mL | | |
| sodium hydroxide, 5N (aq.) | 10 mL | 50 mmol | |
| water | 450 mL | | |
| toluene | 500 mL | | |

The amide-alcohol was dissolved in THF (350 mL) at RT. 2-methoxypropene and methanesulfonic acid were added portionwise, consecutively. The solution was aged for 30 min at RT.

The addition of acid was slightly exothermic, requiring a cooling bath to maintain a temperature below 30° C. The reaction was monitored by HPLC Condition 1 and proceeded to completion (<0.5 A % SM).

Vigorous stirring was required to maintain a slurry.

The thick slurry was transferred portionwise into a sodium hydroxide/water (50 mL) solution at RT. The mixture was extracted with toluene (400 mL) and the layers were separated. The organic layer was washed with water (150 mL) and concentrated to dryness in vacuo for the next reaction.

The basic quench solution must maintain a pH>8 to avoid hydrolysis of the acetonide. The quench is not exothermic.

Step 2: Amino-Phenyl Addition

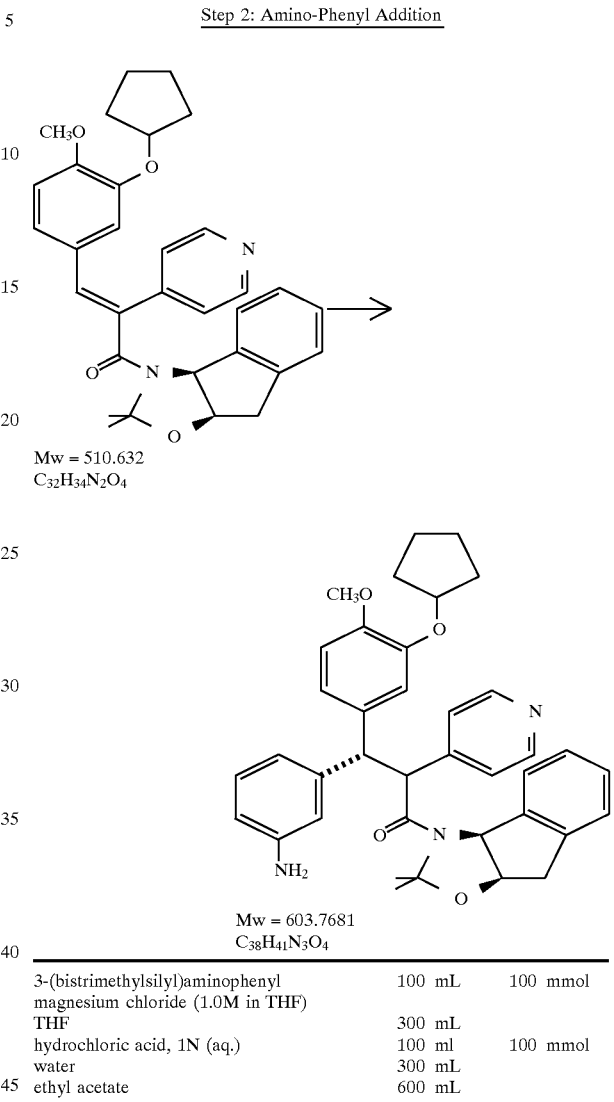

| | | |
|---|---|---|
| 3-(bistrimethylsilyl)aminophenyl magnesium chloride (1.0M in THF) | 100 mL | 100 mmol |
| THF | 300 mL | |
| hydrochloric acid, 1N (aq.) | 100 ml | 100 mmol |
| water | 300 mL | |
| ethyl acetate | 600 mL | |

The acetonide was dissolved in THF (300 mL) and cooled to −25° C. The grignard solution was added over 10 min, maintaining an internal temperature of below −20° C. The solution was aged for 4 h at −20° C.

Grignard is pyrophoric and reacts vigorously with water! The reaction was monitored by HPLC Condition 1 and proceeds to completion.

The solution was warmed to 0° C. and neutralized with hydrochloric acid to pH 7. Water (100 mL) was added and the mixture was aged for 15 min. The mixture was extracted with ethyl acetate (500 mL) and the layers were separated. The aqueous layer was back-extracted with ethyl acetate (100 mL). The combined organic layers were washed with water (200 mL) and concentrated to dryness in vacuo for the next reaction.

Step 3: Acetonide Removal

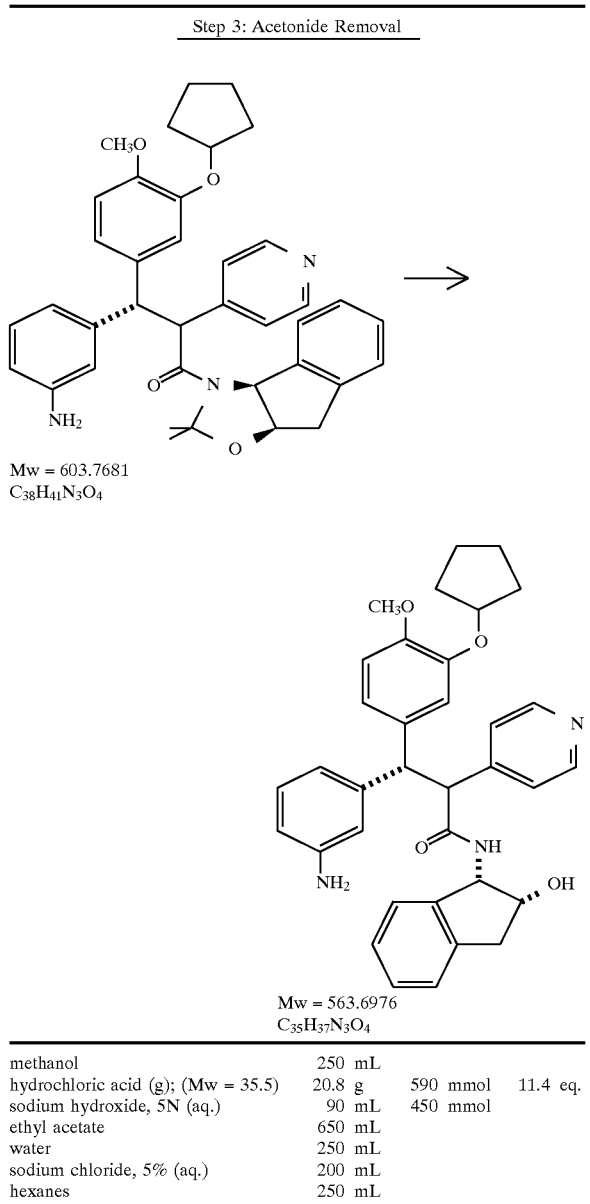

| | | | |
|---|---|---|---|
| methanol | 250 mL | | |
| hydrochloric acid (g); (Mw = 35.5) | 20.8 g | 590 mmol | 11.4 eq. |
| sodium hydroxide, 5N (aq.) | 90 mL | 450 mmol | |
| ethyl acetate | 650 mL | | |
| water | 250 mL | | |
| sodium chloride, 5% (aq.) | 200 mL | | |
| hexanes | 250 mL | | |

Hydrochloric acid gas was bubbled vigorously into the Michael adduct-acetonide/methanol solution at <40° C. in three portions over 1.5 h.

The acid bubbling was exothermic, requiring an ice/water bath to maintain a temperature below 40° C. The reaction was monitored by HPLC Condition 1 and proceeded to completion.

The slurry was neutralized with sodium hydroxide solution (5N, 90 mL) below 30° C. to pH 7.

The neutralization was exothermic, requiring an external cooling bath to maintain a temperature below 40° C.

Water (250 mL) was added, followed by ethyl acetate (500 mL) and THF (100 mL). The layers were separated and the aqueous was back-extracted with ethyl acetate (100 mL). The combined organic layers were washed with 5% aq. NaCl (200 mL) and concentrated to dryness in vacuo, flushing with ethyl acetate (300 mL). The solids were slurrified in ethyl acetate (200 mL) and hexanes (200 mL) was added. The slurry was aged at RT for 30 min. The product was collected by suction filtration as a sandy-brown solid, washing with 1:1 ethyl acetate:hexanes (100 mL) and dried in vacuo at 30° C. for 24 h to give 22.5 g (80% yield) for the three-step conversion.

Step 4: Aminoindanol Hydrolysis

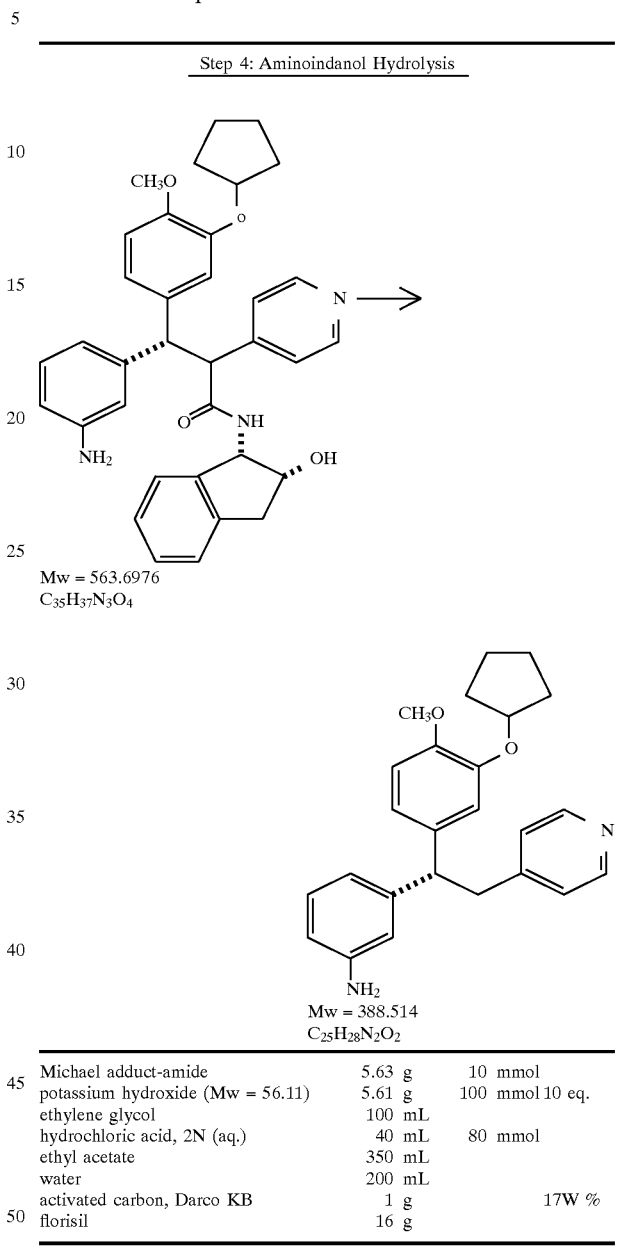

| | | | |
|---|---|---|---|
| Michael adduct-amide | 5.63 g | 10 mmol | |
| potassium hydroxide (Mw = 56.11) | 5.61 g | 100 mmol | 10 eq. |
| ethylene glycol | 100 mL | | |
| hydrochloric acid, 2N (aq.) | 40 mL | 80 mmol | |
| ethyl acetate | 350 mL | | |
| water | 200 mL | | |
| activated carbon, Darco KB | 1 g | | 17W % |
| florisil | 16 g | | |

The amide and potassium hydroxide pellets were suspended in ethylene glycol at RT. The mixture was heated to 160° C. and aged for 15 h. The solution was cooled to 40° C. and neutralized to pH 6.5.

The reaction was monitored by HPLC Condition 1 and proceeded to completion.

The addition of HCl was exothermic, requiring an ice/water bath to maintain a temperature below 40° C.

The mixture was diluted with water (100 mL) and ethyl acetate (150 mL). The layers were separated after mixing for 15 min. The organic layer was washed with water (100 mL). Activated carbon was added to the organic layer and the solution was heated to 60° C. and aged for 1 h. The solution was cooled to 35° C. and filtered through a pad of florisil, using ethyl acetate (200 mL) for washings. The solution was concentrated to dryness in vacuo to give 3.5 g (90% yield) of crude product.

The carbon treatment removed solids and polar impurities, but does not result in a colorless solution.

Assay yield is 85–90%.

The entantiomeric purity of the free amine is 95–96% ee.

What is claimed is:

1. A process for the preparation of a compound of structural formula VIII:

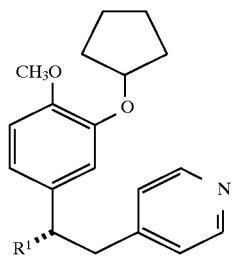

wherein:

R$^1$ is: phenyl, either unsubstituted or substituted with one or two substituents, which can be the same or different, selected from the group consisting of R$^2$ and Alk$^1$(R$^2$)m wherein:

R$^2$ is:
1) —halo,
2) —N(R$^4$)$_2$,
3) —NO$_2$,
4) —CN,
5) —OR$^4$,
6) —C$_{3-6}$ cycloalkoxy,
7) —CO(R$^4$),
8) —COOR$^4$,
9) —SR$^4$,
10) —SO$_3$H,
11) —SO$_2$(R$^4$),
12) —SO$_2$N(R$^4$)$_2$,
13) —CON(R$^4$)$_2$,
14) —NHSO$_2$R$^4$,
15) —N(SO$_2$R$^4$)$_2$,
16) —NHSO$_2$N(R$^4$)$_2$,
17) —NHCOR$^4$ or
18) —NHCOOR$^4$; wherein Alk$^1$ is: straight or branched chain C$_{1-6}$ alkylene, C$_{2-6}$ alkenylene or C$_{2-6}$ alkynylene, optionally interrupted by one, two or three —O—, —S—, —S(O)p or —N(R$^4$)—;

R$^4$ is: hydrogen or C$_{1-6}$ alkyl;

m is: zero or an integer selected from 1, 2 and 3; and p is: an integer selected from 1 and 2 which comprises the steps of:

(a) coupling a compound of formula III:

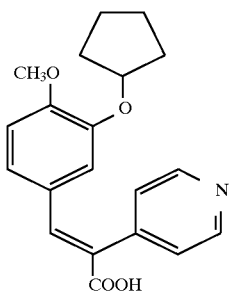

with (1R,2S) cis-aminoindanol in an aprotic solvent in the presence of one or more amide coupling reagents to yield a compound of formula IV:

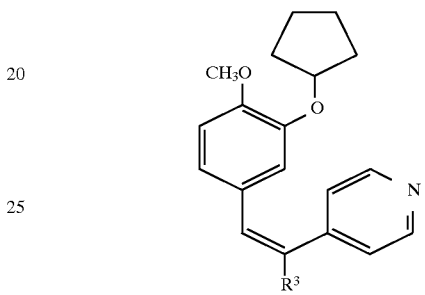

wherein R$^3$ is:

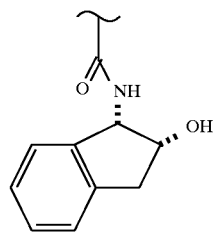

(b) Reacting a compound of formula IV with 2-methoxypropene and methanesulfonic acid in an aprotic solvent to yield a compound of formula V:

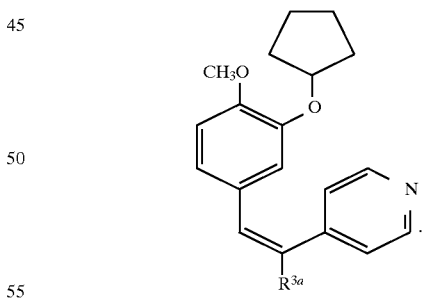

wherein R$^{3a}$ is:

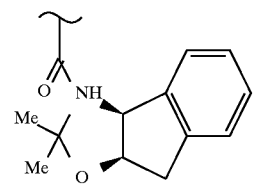

(c) Reacting, by conjugate addition, a compound of formula V with a compound of the formula:

(a) Li R$^1$,
(b) R$^1$MgX, wherein X is halo,
(c) Li (R$^1$)$_2$Cu, or
(d) Li$_2$R$^1$CuCnX in an aprotic solvent to yield, after acidification a compound of formula VI:

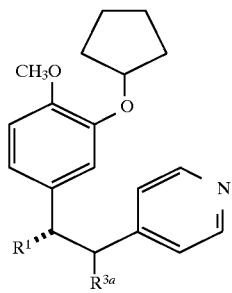

VI (d) Reacting an amide of formula VI with strong acid in a hydrolytic solvent to yield, after neutralization, a compound of formula VII:

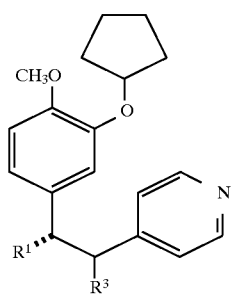

VII (e) Hydrolysis of compound VII with a strong base in a non-reactive water soluble organic solvent to yield a compound of formula VIII:

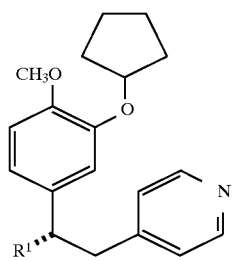

VIII

2. The process of claim 1, wherein R$^1$ is phenyl, or aminophenyl.

3. A process for the preparation of a compound of structural formula VIII:

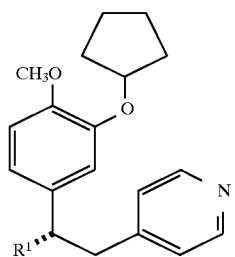

VIII wherein:
R$^1$ is: phenyl, either unsubstituted or substituted with one or two substituents, which can be the same or different, selected from the group consisting of R$^2$ and Alk$^1$ (R$^2$)m wherein:

R$^2$ is:
1) —halo,
2) —N(R$^4$)$_2$,
3) —NO$_2$,
4) —CN,
5) —OR$^4$,
6) —C$_{3-6}$ cycloalkoxy,
7) —CO(R$^4$),
8) —COOR$^4$,
9) —SR$^4$,
10) —SO$_3$H,
11) —SO$_2$(R$^4$),
12) —SO$_2$N(R$^4$)$_2$,
13) —CON(R$^4$)$_2$,
14) —NHSO$_2$R$^4$,
15) —N(SO$_2$R$^4$)$_2$,
16) —NHSO$_2$N(R$^4$)$_2$,
17) —NHCOR$^4$ or
18) —NHCOOR$^4$; wherein Alk$^1$ is: straight or branched chain C$_{1-6}$ alkylene, C$_{2-6}$ alkenylene or C$_{2-6}$ alkynylene, optionally interrupted by one, two or three —O—, —S—, —S(O)p or —N(R$^4$)—;

R$^4$ is: hydrogen or C$_{1-6}$ alkyl;

m is: zero or an integer selected from 1, 2 and 3; and p is: an integer selected from 1 and 2 which comprises the steps of:

(b) Reacting a compound of formula IV

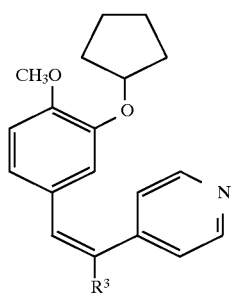

IV wherein R$^3$ is:

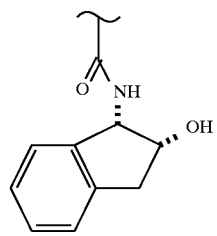

with 2-methoxypropene and methanesulfonic acid in an aprotic solvent to yield a compound of formula V:

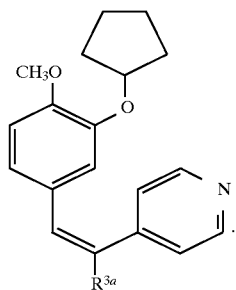

wherein $R^{3a}$ is:

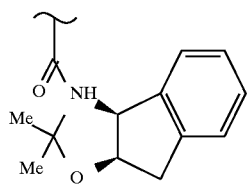

(c) Reacting, by conjugate addition, a compound of formula V with a compound of the formula:

(a) $LiR^1$,
(b) $R^1MgX$, wherein X is halo,
(c) $Li(R^1)_2Cu$, or
(d) $Li_2R^1CuCnX$ in an aprotic solvent to yield, after acidification a compound of formula VI:

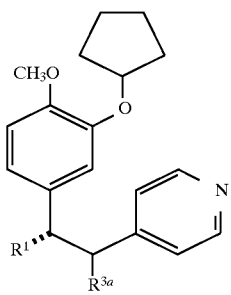

(d) Reacting an amide of formula VI with strong acid in a hydrolytic solvent to yield, after neutralization, a compound of formula VII:

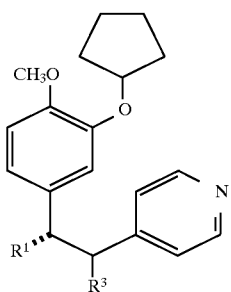

(e) Hydrolysis of compound VII with a strong base in a non-reactive water soluble organic solvent to yield a compound of formula VIII:

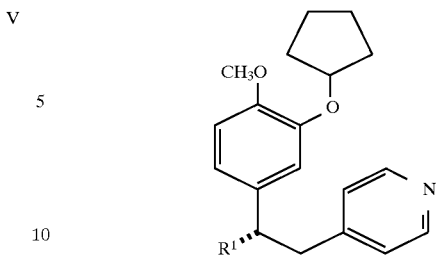

4. The process of claim 3, wherein $R^1$ is phenyl or aminophenyl.

5. A process for the preparation of a compound of structural formula VIII:

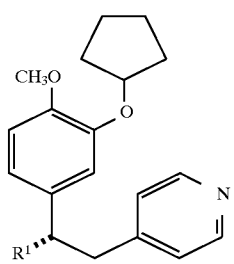

wherein:

$R^1$ is: phenyl, either unsubstituted or substituted with one or two substituents, which can be the same or different, selected from the group consisting of $R^2$ and $Alk^1$ $(R^2)m$ wherein:

$R^2$ is:
1) —halo,
2) —$N(R^4)_2$,
3) —$NO_2$,
4) —CN,
5) —$OR^4$,
6) —$C_{3-6}$ cycloalkoxy,
7) —$CO(R^4)$,
8) —$COOR^4$,
9) —$SR^4$,
10) —$SO_3H$,
11) —$SO_2(R^4)$,
12) —$SO_2N(R^4)_2$,
13) —$CON(R^4)_2$,
14) —$NHSO_2R^4$,
15) —$N(SO_2R^4)_2$,
16) —$NHSO_2N(R^4)_2$,
17) —$NHCOR^4$ or
18) —$NHCOOR^4$; wherein $Alk^1$ is: straight or branched chain $C_{1-6}$ alkylene, $C_{2-6}$ alkenylene or $C_{2-6}$ alkynylene, optionally interrupted by one, two or three —O—, —S—, —S(O)p or —$N(R^4)$—;

$R^4$ is: hydrogen or $C_{1-6}$ alkyl;

m is: zero or an integer selected from 1, 2 and 3; and p is: an integer selected from 1 and 2 which comprises the steps of:

Reacting, by conjugate addition, a compound of formula V

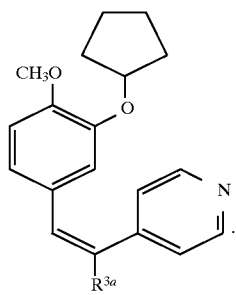

V wherein R³ᵃ is:

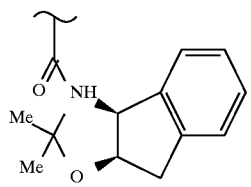

with a compound of the formula:

(a) Li R¹,
(b) R¹MgX, wherein X is halo,
(c) Li (R¹)₂Cu, or
(d) Li₂R¹CuCnX in an aprotic solvent to yield, after acidification a compound of formula VI:

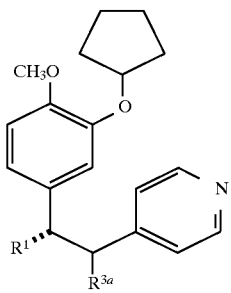

VI (d) Reacting an amide of formula VI with strong acid in a hydrolytic solvent to yield, after neutralization, a compound of formula VII:

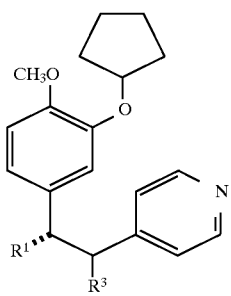

VII wherein R³ is:

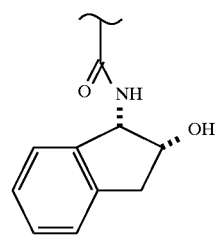

(e) Hydrolysis of compound VII with a strong base in a non-reactive water soluble organic solvent to yield a compound of formula VIII:

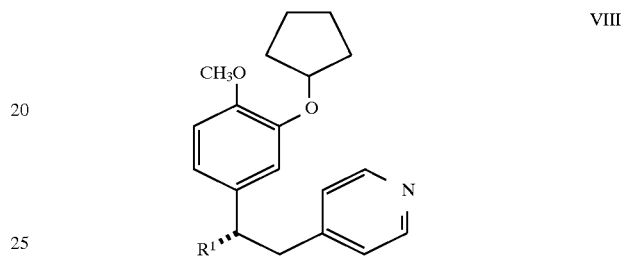

VIII

6. The process of claim 5, wherein R¹ is phenyl or aminophenyl.

7. A process for the preparation of a compound of structural formula VIII:

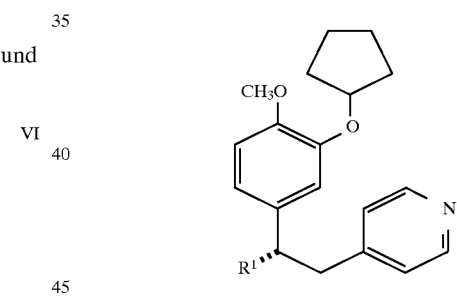

VIII wherein:
R¹ is: phenyl, either unsubstituted or substituted with one or two substituents, which can be the same or different, selected from the group consisting of R² and Alk¹(R²)m wherein:
R² is:
1) —halo,
2) —N(R⁴)₂,
3) —NO₂,
4) —CN,
5) —OR⁴,
6) —C₃₋₆ cycloalkoxy,
7) —CO(R⁴),
8) —COOR⁴,
9) —SR⁴,
10) —SO₃H,
11) —SO₂(R⁴),
12) —SO₂N(R⁴)₂,
13) —CON(R⁴)₂,
14) —NHSO₂R⁴, 15) —N(SO$_2$R$^4$)$_2$,
16) —NHSO$_2$N(R$^4$)$_2$,
17) —NHCOR$^4$ or
18) —NHCOOR$^4$; wherein Alk$^1$ is: straight or branched chain C$_{1-6}$ alkylene, C$_{2-6}$ alkenylene or C$_{2-6}$ alkynylene, optionally interrupted by one, two or three —O—, —S—, —S(O)p or —N(R$^4$)—;

R$^4$ is: hydrogen or C$_{1-6}$ alkyl;

m is: zero or an integer selected from 1, 2 and 3; and p is: an integer selected from 1 and 2 which comprises the steps of:

(d) Reacting an amide of formula VI

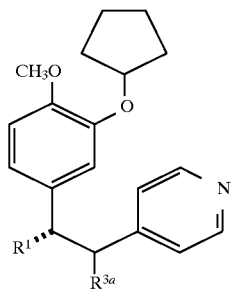
VI wherein R$^{3a}$ is:

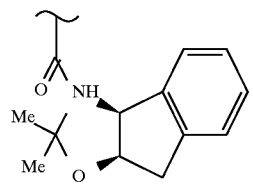

with strong acid in a hydrolytic solvent to yield, after neutralization, a compound of formula VII:

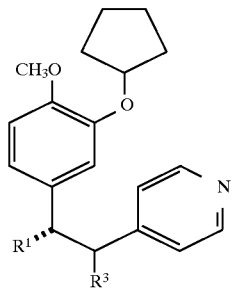
VII wherein R$^3$ is:

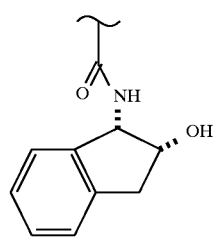

(e) Hydrolysis of compound VII with a strong base in a non-reactive water soluble organic solvent to yield a compound of formula VIII:

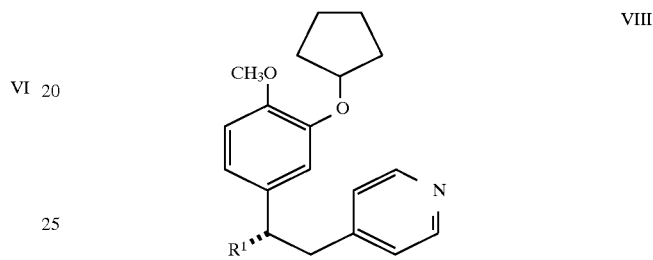
VIII

8. The process of claim 7, wherein R$^1$ is phenyl or aminophenyl.

9. A process for the preparation of a compound of structural formula VIII:

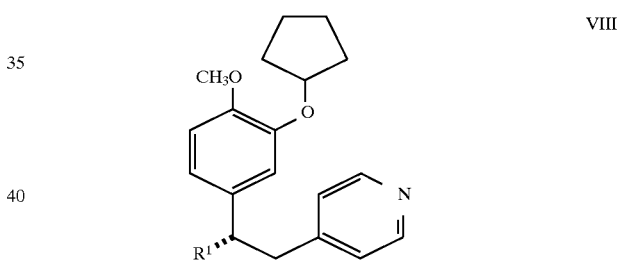
VIII wherein:

R$^1$ is: phenyl, either unsubstituted or substituted with one or two substituents, which can be the same or different, selected from the group consisting of R$^2$ and Alk$^1$(R$^2$)m wherein:

R$^2$ is:
1) —halo,
2) —N(R$^4$)$_2$,
3) —NO$_2$,
4) —CN,
5) —OR$^4$,
6) —C$_{3-6}$ cycloalkoxy,
7) —CO(R$^4$),
8) —COOR$^4$,
9) —SR$^4$,
10) —SO$_3$H,
11) —SO$_2$(R$^4$),
12) —SO$_2$N(R$^4$)$_2$,
13) —CON(R$^4$)$_2$,
14) —NHSO$_2$R$^4$,
15) —N(SO$_2$R$^4$)$_2$, 16) —NHSO₂N(R⁴)₂,
17) —NHCOR⁴ or
18) —NHCOOR⁴; wherein Alk¹ is: straight or branched chain $C_{1-6}$ alkylene, $C_{2-6}$ alkenylene or $C_{2-6}$ alkynylene, optionally interrupted by one, two or three —O—, —S—, —S(O)p or —N(R⁴)—;

R⁴ is: hydrogen or $C_{1-6}$ alkyl;

m is: zero or an integer selected from 1, 2 and 3; and p is: an integer selected from 1 and 2 which comprises:

(e) Hydrolysis of compound VII

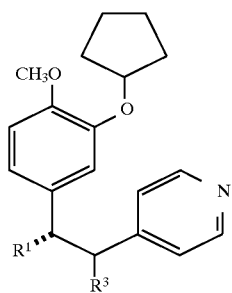

VII wherein R³ is:

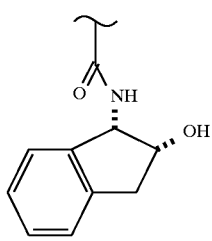

with a strong base in a non-reactive water soluble organic solvent to yield a compound of formula VIII:

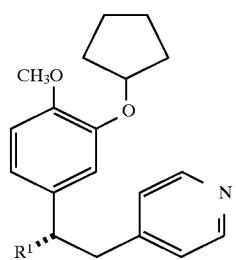

VIII

10. The process of claim 9, wherein R¹ is phenyl or aminophenyl.

* * * * *